United States Patent
Williams et al.

(10) Patent No.: US 8,483,794 B2
(45) Date of Patent: Jul. 9, 2013

(54) METHOD FOR IMPLANTING AN ELECTRODE THAT UNFURLS IN RESPONSE TO A PREDETERMINED STIMULUS

(71) Applicant: Wisconsin Alumni Research Foundation, Madison, WI (US)

(72) Inventors: Justin C. Williams, Cambridge, WI (US); Karl A. Sillay, Madison, WI (US); Jiwan Kim, Madison, WI (US); David Niemann, Madison, WI (US); Azam Ahmed, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/716,612

(22) Filed: Dec. 17, 2012

(65) Prior Publication Data

US 2013/0110193 A1    May 2, 2013

Related U.S. Application Data

(62) Division of application No. 12/275,696, filed on Nov. 21, 2008, now Pat. No. 8,386,007.

(51) Int. Cl.
*A61B 5/04*  (2006.01)
*A61N 1/00*  (2006.01)

(52) U.S. Cl.
USPC ........... 600/378; 600/377; 600/544; 600/545; 607/116

(58) Field of Classification Search
USPC ......... 600/373, 377–378, 393, 395, 544–545; 607/115–118
See application file for complete search history.

(56) References Cited

U.S. PATENT DOCUMENTS

| | | | |
|---|---|---|---|
| 6,171,239 | B1 | 1/2001 | Humphrey |
| 6,324,429 | B1 | 11/2001 | Shire et al. |
| 6,330,466 | B1 | 12/2001 | Hofmann et al. |
| 7,259,503 | B2 | 8/2007 | Pei et al. |
| 2003/0100823 | A1 | 5/2003 | Kipke et al. |
| 2004/0054276 | A1 | 3/2004 | Finneran et al. |
| 2009/0018630 | A1 | 1/2009 | Osypka et al. |
| 2009/0130423 | A1 | 5/2009 | Keady |
| 2009/0177261 | A1 | 7/2009 | Teoh et al. |
| 2010/0145427 | A1 | 6/2010 | Gliner et al. |

OTHER PUBLICATIONS

"A Cortical Recording Platform Utilizing uECoG Electrode Arrays", Proceedings of the 29th Annual International Conference of the IEEE EMBS, Cite Interantionale, Lyon, France, Aug. 23-26, 2007, pp. 5353-5357, by Jiwan Kim, J. Adam Wilson, and Justin C. Williams.
"3-D Silicon Probe Array With Hybrid Polymer Interconnect For Chronic Cortical Recording," Proceedings of the 1st International IEEE EMS, Conference of Neural Engineering, Capri Island, Italy, Mar. 20-22, 2003, pp. 181-184, by J. F. Hetke, J. C. Williams, D. S. Pellinen, R. J. Vetter and D.R. Kipke.
"Flexible Polyimide-Based Intracortical Electrode Arrays With Bioactive Capability," IEEE Transactions on Biomedical Engineering, vol. 48, No. 3, Mar. 2001, by Patrick J. Rousche, David S. Pellinen, David P. Pivin, Jr., Justin C. Williams, Rio J. Vetter and Daryl R. Kipke.

*Primary Examiner* — Linda Dvorak
*Assistant Examiner* — Brian M Antiskay
(74) *Attorney, Agent, or Firm* — Boyle Fredrickson S.C.

(57) ABSTRACT

A thin-film microelectrode array tailored for long-term, minimally invasive cortical recording or stimulation and method are provided. The microelectrode array includes a flexible element that is movable between a first contracted configuration and a second expanded configuration. An array of contacts is provided on the flexible element. The contacts are engagable with a cortical surface with the flexible element in the expanded configuration. A link operatively connects the array of contacts to a control module. The link is capable of transmitting at least one of cortical recordings and cortical stimulation signals thereon.

7 Claims, 3 Drawing Sheets

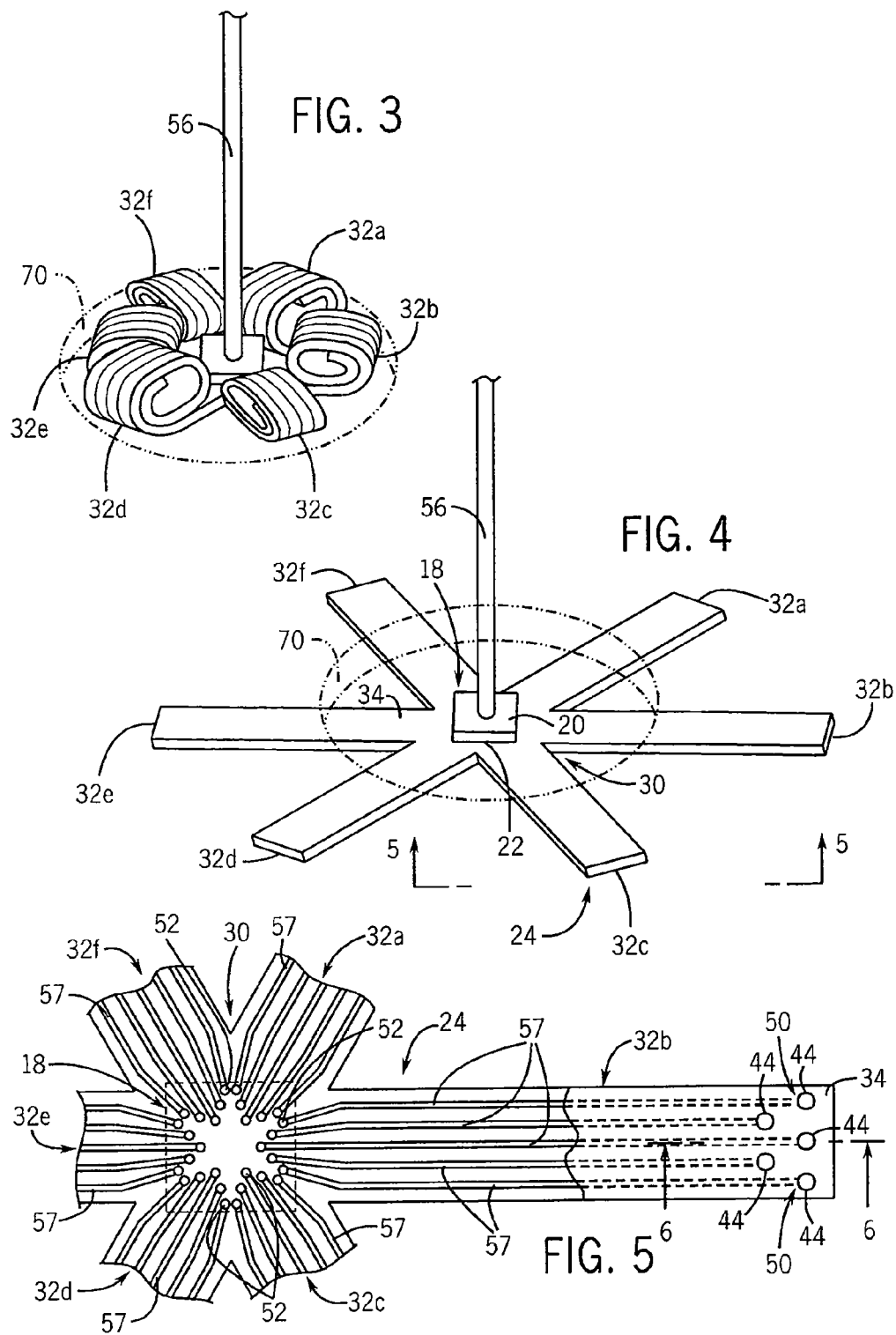

METHOD FOR IMPLANTING AN ELECTRODE THAT UNFURLS IN RESPONSE TO A PREDETERMINED STIMULUS

CROSS-REFERENCE TO RELATED APPLICATION

This application is divisional of U.S. Ser. No. 12/275,696, filed Nov. 21, 2008.

REFERENCE TO GOVERNMENT GRANT

This invention was made with government support under RR023268 and NS044287 awarded by the National Institutes of Health. The government has certain rights in this invention.

FIELD OF THE INVENTION

This invention relates generally to brain-computer interface technology, and in particular, to a thin-film microelectrode array that is tailored specifically for long-term, minimally invasive cortical recording or stimulation and method for implanting the same.

BACKGROUND AND SUMMARY OF THE INVENTION

Recently, brain-computer interface (BCI) technology, particularly with regards to neuroprosthetics, has become a common area of interest in the neuro-engineering realm. Accelerated interdisciplinary research has been achieved by the collaboration between neuroscience, medicine, and rehabilitation engineering, bringing the common goal of technology for treating severe motor impairment closer to reality. This endeavor has also shown potential in the elucidation of the neural mechanisms inherent in the central nervous system. Devices for brain signal acquisition, essential components of BCI systems, have lead to a plethora of novel bio-signal acquisition modalities. For example, clinical cortical monitoring devices are routinely utilized for monitoring and mapping epilepsy activity. Recording and interpreting electrical signals from the cortex has been used for BCIs, which can enhance communication for individuals with conditions such as spinal cord injury or amyotrophic lateral sclerosis (ALS). In addition, therapeutic stimulation has been used for stroke rehabilitation, alleviation of chronic pain, and seizure control.

The Electroencephalogram (EEG) has been the primary focus of clinical BCI technology thus far, due to its safety and convenience. However, EEG signals lack the resolution, amplitude, and bandwidth offered by more invasive methods. Various invasive microelectrode arrays such as Michigan probes and the Utah electrode arrays have been developed within the last 20 years to achieve more localized neural signals. Since these devices are based on silicon microfabrication technology, with micron scale features, they are capable of detecting single neuron activity. Though their capability to detect minute changes in action potentials is very impressive, inserting the probes arrays into brain tissue can cause significant scar tissue accumulation around the device (cell encapsulation/ensheathing), which may decrease the intensity of signal and the signal to noise ratio (SNR), and can lead to a loss of recording ability.

Recent Electrocorticogram (ECoG) studies have shown promise for its use as an alternative method for BCI control. Unlike invasive electrodes requiring penetration into the cortex, ECoG electrodes are placed on the cortex surface, which can reduce risk of possible implant related damage. ECoG also has some advantages over EEG including higher spatial resolution, broader bandwidth and higher amplitude than EEG. Recent studies have shown that ECoG signals can be used for BCI control with minimum training and they contain detailed aspects of motor actions, which was previously thought to be only possible using invasive electrodes. However, these devices are much larger than necessary and made with sub-optimal materials. In addition, there are issues of compatibility of the device in physiological environments.

Therefore, it is a primary object and feature of the present invention to provide a thin-film microelectrode array that is tailored specifically for long-term, minimally invasive cortical recording or stimulation.

It is a further object and feature of the present invention to provide a thin-film microelectrode array that has an improved signal-to-noise ratio and higher spatial resolution over the current electrode modalities.

It is a still further object and feature of the present invention to provide a thin-film microelectrode array that is simple and inexpensive to fabricate.

In accordance with the present invention, an electrode is provided that is tailored for long-term, minimally invasive cortical recording or stimulation. The electrode includes a flexible element having first and second sides. The flexible element is movable between a first contracted configuration and a second expanded configuration. A contact is received in the second side of the flexible element. The contact is engagable with a cortical surface with the flexible element in the expanded configuration. A link operatively connects the contact to a control module. The link is capable of transmitting at least one of cortical recordings and cortical stimulation signals thereon.

The second side of the flexible element may be hydrophilic and the first side of the flexible element may be hydrophobic. The flexible element moves between the contracted configuration and the expanded configuration in response to a predetermined stimulus. It is contemplated for the predetermined stimulus to be voltage. A cable has a first end operatively connected to the contact and a second end connectable to the control module. A second contact may be engagable with a cortical surface with the flexible element in the expanded configuration.

In accordance with a further aspect of the present invention, a thin-film microelectrode array is provided that is tailored for long-term, minimally invasive cortical recording or stimulation. The electrode includes a flexible element that is movable between a first contracted configuration and a second expanded configuration. An array of contacts is provided on the flexible element. The contacts are engagable with a cortical surface with the flexible element in the expanded configuration. A link operatively connects the array of contacts to a control module. The link is capable of transmitting at least one of cortical recordings and cortical stimulation signals thereon.

The flexible element includes first and second sides. The second side of the flexible element may be hydrophilic and the first side of the flexible element may be hydrophobic. The flexible element moves between the contracted configuration and the expanded configuration in response to a predetermined stimulus. It is contemplated for the predetermined stimulus to be voltage. The link may include a plurality of lines. Each line has a first end operatively connected to one of the array of contacts and a second end connectable to the control module.

In accordance with a still further aspect of the present invention, a method is provided for implanting an electrode having an array of contacts on a cortical surface. The method includes the step of positioning the electrode on the cortical surface. The electrode is movable between a first contracted configuration and a second expanded configuration. Thereafter, the electrode is unfurled from the contracted configuration to the expanded configuration such that the array of contacts engages the cortical surface.

The method may include additional step of transmitting cortical recordings from the array of contacts to a control module. Alternatively, the method may include the step of transmitting cortical stimulation signals to the array of contacts. The electrode includes first and second sides. The second side of the flexible element may be hydrophilic and the first side of the flexible element may be hydrophobic. The step of unfurling the electrode may include the additional step of applying a predetermined stimulus to the electrode. It is contemplated for the predetermined stimulus to be voltage. It is also contemplated for the method to include the additional step of operatively connecting the array of contacts to a control module.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings:

FIG. 3 is an isometric view of the microelectrode array of the present invention in a first, retracted configuration;

FIG. 4 is an isometric view of the microelectrode array of the present invention in a second, expanded;

FIG. 5 is a bottom plan view, partially in section, of the microelectrode array of the present invention taken along line 5-5 of FIGS. 4.

DETAILED DESCRIPTION OF THE DRAWINGS

Figure 1:
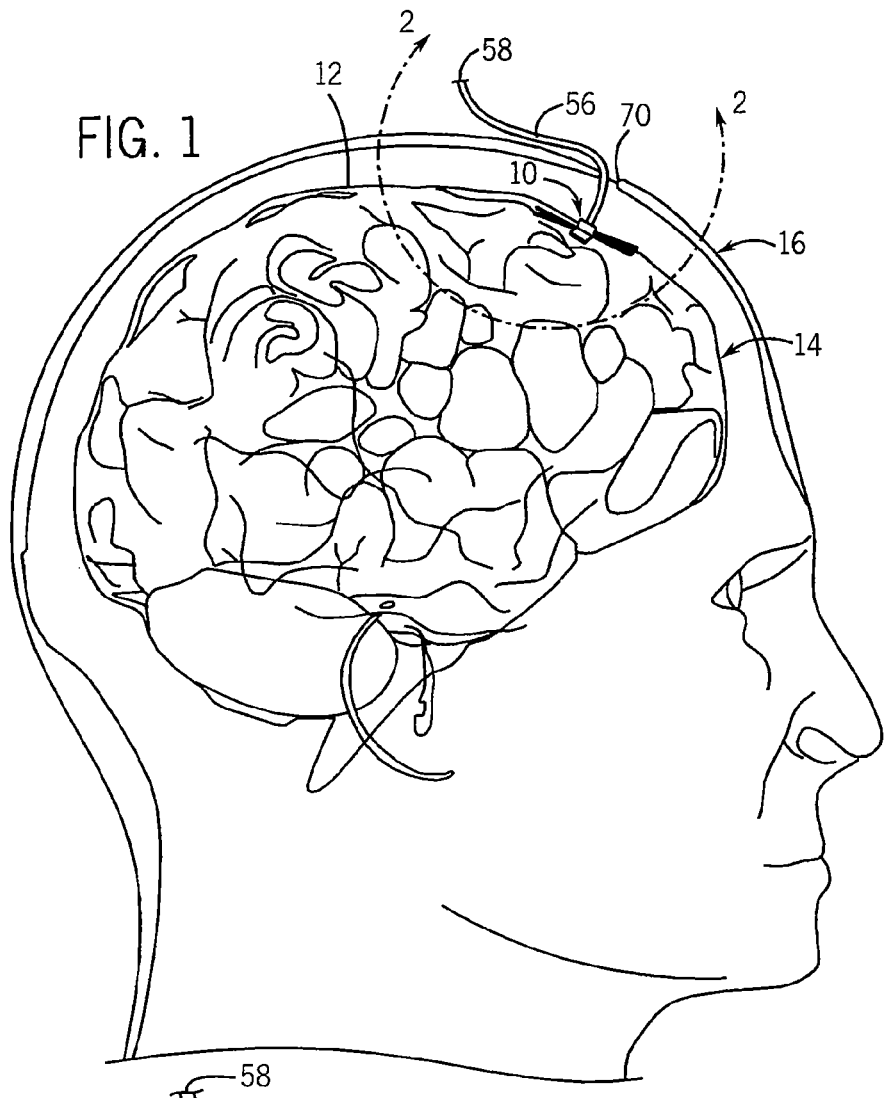
FIG. 1 is an isometric view of a microelectrode array in accordance with the present invention implanted on a surface of a human brain.

Referring to FIG. 1, a thin-film microelectrode array in accordance with the present invention is generally designated by the reference numeral 10. It is intended that microelectrode array 10 be implanted on surface 12 of brain 14 within cranium 16. It can be appreciated that microelectrode array 10 may be implanted within cranium 16 of an animal or a human without deviating from the scope of the present invention. Further, it can be appreciated microelectrode array 10 may be adapted for implantation on the surface of other parts of a body, both internal and external, without deviating from the scope of the present invention.

Figure 2:
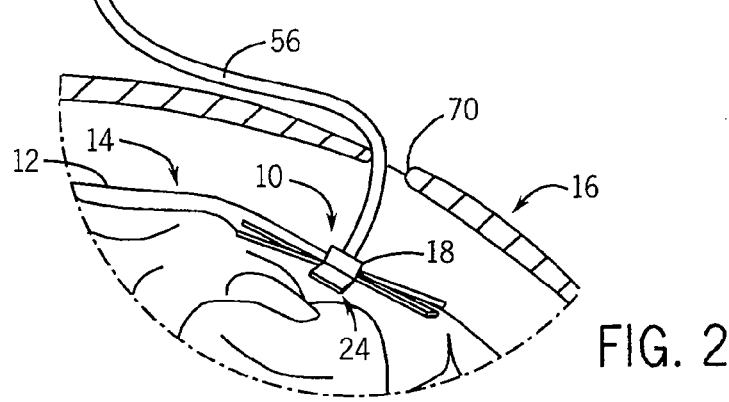
FIG. 2 is an enlarged, isometric view of the microelectrode array of the present invention taken along line 2-2 of FIG. 1.

Referring to FIGS. 2-4, an exemplary configuration of a microelectrode array in accordance with the present invention is depicted. It can be appreciated that microelectrode array 10 may have other configurations without deviating from the scope of the present invention. In the depicted embodiment, microelectrode array 10 includes base 18 having a generally square configuration. Base 18 includes upper and lower surfaces 20 and 22, respectively, and is formed from a biocompatible polymer. Electrode structure 24 is mounted to lower surface 22 of base 18. More specifically, electrode structure 24 includes first and second layers 26 and 28, respectively, fabricated from flexible, biocompatible polymers, FIG. 6. First and second layers 26 and 28, respectively, are defined by upper surfaces 34 and 36, respectively, and lower surfaces 38 and 40, respectively. Lower surface 38 of first layer 26 is affixed to upper surface 36 of second layer 28 in any conventional manner. In the depicted environment, electrode structure 24 includes a central portion 30 having a plurality of spokes 32a-32f extending radially therefrom. Upper surface 34 of first layer 26 of central portion 30 of electrode structure 24 is secured to lower surface 22 of base 18, for reasons hereinafter described.

Figure 6:
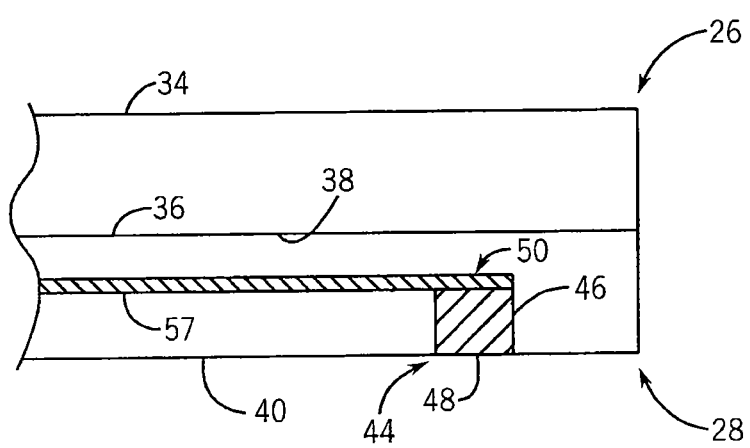
FIG. 6 is a cross-sectional view of the microelectrode array of the present invention taken along line 6-6 of FIG. 5.

Referring to FIGS. 5-6, lower surface 40 of second layer 28 of the plurality of spokes 32a-32f of electrode structure 24 includes a plurality of contacts 44 formed therein. Contacts 44 may take the form of contact pads 46 having terminal ends 48 generally co-planar with lower surface 40 of second layer 28 of the plurality of spokes 32a-32f of electrode structure 24. Alternatively, contacts 44 may take the form of elongated contact strips having contact surfaces generally co-planar with lower surface 40 of second layer 28 of the plurality of spokes 32a-32f of electrode structure 24. As best seen in FIG. 5, contacts 44 are operatively connected to a corresponding electrode lead wires housed within electrode lead 56 by trace wires 57. More specifically, each trace wire 57 has a first end 50 operatively connected to a corresponding contact 44 and second end 52 electrically coupled to terminal ends of corresponding electrodes lead wires housed within electrode lead 56. Electrode lead 56 extends from upper surface 20 of base 18 and terminates at terminal end 58. Terminal end 58 of electrode lead 56 is connectable to a central processing unit, for reasons hereinafter described.

As heretofore described, first and second layers 26 and 28, respectively, are fabricated from flexible materials. The flexibility of first and second layers 26 and 28, respectively, allows the plurality of spokes 32a-32f of electrode structure 24 to be movable between a first retracted position, FIG. 3, wherein each of the plurality of spokes 32a-32f of electrode structure 24 is folded onto itself and a second extended configuration wherein each of the plurality of spokes 32a-32f of electrode structure 24 extends radially from central portion 30 of electrode structure 24. With plurality of spokes 32a-32f of electrode structure 24 in the extended configuration, the flexibility of first and second layers 26 and 28, respectively, provides stronger relief against the forces of micro motion between the tissue of the brain 14 and microelectrode array 10.

In addition, it is contemplated for the chemistry of lower surface 40 of second layer 28 to allow for a host of bioactive organic species to be either absorbed or covelantly bonded thereto. The flexibility and bioactivity of lower surface 40 of second layer 28 are intended to provide an optimal implant environment and extend the time period that microelectrode array 10 may be maintained within cranium 16 without inducing excessive foreign body or immune response. It is also contemplated for upper surface 34 of first layer 26 to be hydrophobic and for lower surface 40 of second layer 28 to be hydrophilic. As a result, lower surface 40 of second layer 28 is drawn to and maintains contact with surface 12 of brain 14 as microelectrode array 10 is unfurled from the retracted position, FIG. 3, to the expanded configuration, FIGS. 1-2 and 4.

In order to unfurl microelectrode array 10 from the retracted position, FIG. 3, to the expanded configuration, FIGS. 1-2 and 4, first layer 26 may be fabricated from an electroactive polymer. As is known, electroactive polymers change shape in response to the application of voltage thereto.

However, it can be appreciated that other mechanisms may be used to unfurl microelectrode array 10. For example, first layer 26 may be fabricated from a temperature sensitive polymer that expands in response to exposure to a predetermined temperature, thereby unfurling microelectrode array 10 from the retracted position, FIG. 3, to the expanded configuration, FIGS. 1-2 and 4.

In operation, microelectrode array 10 is inserted though opening 70 in cranium 16 of an individual such that lower surface 40 of central portion 30 of second layer 28 is positioned against brain 14. The plurality of spokes 32a-32f of electrode structure 24 of microelectrode array 10 are unfurled to their expanded configurations such that contact pads 46 are positioned adjacent target neurons on surface 12 of brain 14. Apertures (not shown) may extend through the plurality of spokes 32a-32f of electrode structure 24 to make microelectrode array 10 porous, and as such, increase the biocompatibility between microelectrode array 10 and brain 14. Further, it is contemplated to provide chemicals, drugs or other stimuli within such apertures to further enhance the biocompatibility of microelectrode array 10 and brain 14 or to treat various neurological disorders.

In order to monitor the inner cranial field potentials associated with the target neurons in the brain, terminal end 58 of electrode lead 56 is electrically coupled to the central processing unit via an analog-to-digital converter. The analog-to-digital converter receives analog signals corresponding to cortical stimulation signals, such as the intracranial field potentials of the target neurons detected by contact pads 46, and converts the signals to a digital format. The digital signals are transmitted to and filtered by a filter and provided to the central processing unit for further processing. Alternatively, the central processing unit may transmit cortical stimulation signals to contact pads 46 via electrode lead 56.

As described, microelectrode array 10 of the present invention is less invasive compared to conventional electrodes from surgical prospective. More specifically, microelectrode array 10 of the present invention is more flexible; has a better signal to noise ratio; and is more biocompatible then conventional electrodes. As a result, microelectrode array 10 of the present invention is more adapted for chronic use and can be implanted in patients for a considerably longer period of time than conventional electrodes.

It is understood that the configuration of microelectrode array 10 is merely exemplary. By way of example, microelectrode array 10 may be coiled as a spiral with microelectrode array 10 in its retracted configuration such that microelectrode array 10 may be wrapped around a catheter during implantation. Alternatively, microelectrode array 10 may be housed within a catheter during implantation and deployed from the interior thereof. As such, the catheter may be used to navigate microelectrode array 10 over the convoluted surface of the brain and to avoid bridging vessels.

Various modes of carrying out the invention are contemplated as being within the scope of the following claims particularly pointing out and distinctly claiming the subject matter, which is regarded as the invention.

We claim:

1. A method for implanting an electrode having an array of contacts on a cortical surface, comprising the steps of: positioning the electrode on the cortical surface, the electrode: including a first layer fabricated from a first material responsive to a predetermined stimulus and a second layer including the array of contacts, the second layer being operatively connected to the first layer and fabricated from a second material; and being movable between a first contracted configuration and a second expanded configuration; applying a predetermined stimulus to the first layer of the electrode; and unfurling the electrode from the contracted configuration to the expanded configuration in response to the predetermined stimulus such that the array of contacts engages the cortical surface.

2. The method of claim 1 comprising an additional step of transmitting cortical recordings from the array of contacts to a control module.

3. The method of claim 1 comprising an additional step of transmitting cortical stimulation signals to the array of contacts.

4. The method of claim 1 wherein the electrode includes first and second sides, the second side of the electrode being hydrophilic.

5. The method of claim 1 wherein the electrode includes first and second sides, the first side of the electrode being hydrophobic.

6. The method of claim 1 wherein the predetermined stimulus is voltage.

7. The method of claim 1 comprising the additional step of operatively connecting the array of contacts to a control module.

* * * * *